US011304767B2

United States Patent
Rus et al.

(10) Patent No.: US 11,304,767 B2
(45) Date of Patent: Apr. 19, 2022

(54) ORIGAMI ROBOTS, SYSTEMS, AND METHODS OF TREATMENT

(71) Applicants: Massachusetts Institute of Technology, Cambridge, MA (US); Children's Medical Center Corporation, Boston, MA (US)

(72) Inventors: Daniela Rus, Weston, MA (US); Shuhei Miyashita, Sheffield (GB); Dana Damian, Sheffield (GB)

(73) Assignee: Massachusetts Institute of Technology, Cambridge, MA (US)

( * ) Notice: Subject to any disclaimer, the term of this patent is extended or adjusted under 35 U.S.C. 154(b) by 329 days.

(21) Appl. No.: 16/592,171

(22) Filed: Oct. 3, 2019

(65) Prior Publication Data
US 2020/0038061 A1 Feb. 6, 2020

Related U.S. Application Data

(62) Division of application No. 15/493,956, filed on Apr. 21, 2017, now Pat. No. 10,470,799.
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/52* (2013.01); *A61B 34/72* (2016.02); *A61B 34/73* (2016.02);
(Continued)

(58) Field of Classification Search
CPC ............ A61M 31/002; A61M 2205/35; A61M 2205/3507; A61M 2205/3515;
(Continued)

(56) References Cited

U.S. PATENT DOCUMENTS 5,364,404 A * 11/1994 Jaffe ...................... A61B 17/52
606/106
5,431,640 A 7/1995 Gabriel
(Continued)

OTHER PUBLICATIONS

Miyashita, et al., "An Untethered Miniature Origami Robot that Self-folds, Walks, Swims, and Degrades", 2015 IEEE International Conference on Robotics and Automation (ICRA).
(Continued)

*Primary Examiner* — James D Ponton
(74) *Attorney, Agent, or Firm* — Eversheds Sutherland (US) LLP

(57) ABSTRACT

Origami robots, and associated systems, methods of treatment, and methods of manufacture are provided. A system includes an origami robot encapsulated for ingestion by a patient, such as in a biocompatible material that is dissolvable or meltable within the gastrointestinal tract. A method of treatment includes delivering an origami robot in a folded position into a gastrointestinal tract of a patient, causing the origami robot to unfold within the gastrointestinal tract, and directing the origami robot to a site requiring treatment in the gastrointestinal tract.

17 Claims, 6 Drawing Sheets

Related U.S. Application Data

(60) Provisional application No. 62/325,665, filed on Apr. 21, 2016.

(51) Int. Cl.
*A61B 17/52* (2006.01)
*A61M 31/00* (2006.01)
*A61B 17/00* (2006.01)

(52) U.S. Cl.
CPC ... *A61M 31/00* (2013.01); *A61B 2017/00004* (2013.01); *A61B 2017/00526* (2013.01); *A61B 2034/303* (2016.02); *A61M 2210/1042* (2013.01)

(58) Field of Classification Search
CPC ......... A61M 2205/3538; A61B 5/4839; A61B 17/52; A61B 34/30; A61B 34/72; A61B 34/73; A61B 2034/302; A61B 2034/303
See application file for complete search history.

(56) References Cited

U.S. PATENT DOCUMENTS

| | | | |
|---|---|---|---|
| 5,431,915 | A | 7/1995 | Harvey et al. |
| 6,263,230 | B1 | 7/2001 | Haynor et al. |
| 6,758,840 | B2 | 7/2004 | Knox |
| 7,169,104 | B2 | 1/2007 | Ueda et al. |
| 7,211,094 | B2 | 5/2007 | Gannoe et al. |
| 8,452,377 | B2 | 5/2013 | Reinschke |
| 8,551,506 | B2 | 10/2013 | Boyden et al. |
| 8,793,075 | B2 | 7/2014 | Boyden et al. |
| 2004/0265359 | A1 | 12/2004 | Sacks et al. |
| 2007/0270629 | A1 | 11/2007 | Charles |
| 2009/0299142 | A1 | 12/2009 | Uchiyama et al. |
| 2010/0030185 | A1* | 2/2010 | Hood ............... A61M 5/14276 604/500 |
| 2011/0282165 | A1 | 11/2011 | Kawano et al. |
| 2012/0035437 | A1 | 2/2012 | Ferren et al. |
| 2012/0053619 | A1* | 3/2012 | Schewe ............. A61B 17/0057 606/213 |
| 2013/0110137 | A1* | 5/2013 | Nicolo .................. A61L 27/227 606/151 |
| 2015/0238517 | A1 | 8/2015 | Imran |
| 2016/0058322 | A1 | 3/2016 | Brister et al. |
| 2017/0106099 | A1* | 4/2017 | Bellinger ............... A61K 47/34 |

OTHER PUBLICATIONS

Harada, Kanako et al., "Wireless Reconfigurable Modules for Robotic Endoluminal Surgery", IEEE International Conference on Robotics and Automation, Kobe, Japan (2009), pp. 2699-2704.
Carpi, Federico et al., "Magnetic Maneuvering of Endoscopic Capsules by Means of a Robotic Navigation System", IEEE Transactions on Biomedical Engineering, vol. 56, No. 5, May 2009, pp. 1482-1490.
Nokata, Makoto et al., "Capsule Type Medical Robot with Magnetic Drive in Abdominal Cavity", Proceedings of the 2nd Biennial IEEE/RAS-EMBS International Conference on Biomedical Robotics and Biomechatronics, Scottsdale, AZ, (2008), pp. 348-353.
Fusco, Stefano et al., "Shape-Switching Microrobots for Medical Applications: The Influence of Shape in Drug Delivery and Locomotion", ACS Applied Materials & Interfaces 7, (2015), pp. 6803-6811.
Glass, Paul et al., "A Legged Anchoring Mechanism for Capsule Endoscopes Using Micropatterned Adhesives", IEEE Transactions on Biomedical Engineering, vol. 55, No. 12, Dec. 2008, pp. 2759-2767.
Hauert, Sabine et al., "Mechanisms of Cooperation in Cancer Nanomedicine: Towards Systems Nanotechnology", Trends Biotechnol. 32(9), Sep. 2014, pp. 448-455.
Nelson, Bradley J. et al., "Microrobots for Minimally Invasive Medicine", Annu. Rev. Biomed. Eng. 12 (2010), pp. 55-85.
Moglia, Andrea et al., "Wireless capsule endoscopy: from diagnostic devices to multipurpose robotic systems", Biomed Microdevices 9 (2007) pp. 235-243.
Miyashita, Shuhei et al., "Self-pop-up Cylindrical Structure by Global Heating", IEEE/RS International Conference on Intelligent Robots and Systems (IROS), 2013, pp. 4065-4071.
Kuribayashi, Kaori et al., "Self-deployable origami stent grafts as a biomedical application of Ni-rich TiNi shape memory alloy foil", Materials Science and Engineering A 419 (2006), pp. 131-137.
Yim, Sehyuk et al., "Biopsy using a Magnetic Capsule Endoscope Carrying, Releasing, and Retrieving Untethered Microgrippers", IEEE Trans. Biomed Eng. (2014) 61(2), pp. 513-521.
Yim, Sehyuk et al., "Magnetically Actuated Soft Capsule With the Multimodal Drug Release Function", IEEE ASME Trans Mechatron. (2013) 18(4), pp. 1413-1418.
Yim, Sehyuk et al., "Design and Rolling Locomotion of a Magnetically Actuated Soft Capsule Endoscope", IEEE Transactions on Robotics, vol. 28, No. 1 (2012), pp. 183-194.
Kummer, Michael P. et al., "OctoMag: An Electromagnetic System for 5-DOF Wireless Micromanipulation", IEEE Transactions on Robotics, vol. 26, No. 6 (2010) pp. 1006-1017.
Damian, Dana D. et al., "Robotic Implant to Apply Tissue Traction Forces in the Treatment of Esophageal Atresia", 2014 IEEE International Conference on Robotics & Automation (ICRA) Hong Kong Convention and Exhibition Center (2014), pp. 786-792.
Kassim, Irwan et al., "Locomotion Techniques for Robotic Colonoscopy", IEEE Engineering in Medicine and Biology Magazine, May/Jun. 2006, pp. 49-56.
International Search Report and Written Opinion, PCT/US2017/028893, 16 pages, Jul. 7, 2017.
Massachusetts Institute of Technology (MIT): "Robot Origami: Robot self-folds, walks, and completes tasks", Jun. 11, 2015, p. 1, XP054977482, retrieved from the internet: URL:https://www.youtube.com/watch?v=ZVYz7G-qLjs [retreived on Jun. 27, 2007].

* cited by examiner

ORIGAMI ROBOTS, SYSTEMS, AND METHODS OF TREATMENT

CROSS-REFERENCE TO RELATED APPLICATIONS

This application is a divisional of U.S. patent application Ser. No. 15/493,956, filed Apr. 21, 2017, which claims priority benefit of U.S. Provisional Application No. 62/325,665, filed on Apr. 21, 2016, the disclosures of which are incorporated by reference herein.

STATEMENT REGARDING FEDERALLY SPONSORED RESEARCH

This invention was made with Government support under Grant Nos. EFRI-1240383 and CCF-1138967 awarded by the National Science Foundation. The Government has certain rights in the invention.

BACKGROUND

The present disclosure generally pertains to devices, systems, and methods for treatment of the gastrointestinal tract, and more specifically pertains to origami robots and associated systems and methods for treatment of the gastrointestinal tract.

It is reported that more than 3500 people of all ages ingest button batteries in the United States every year. 42 deaths and 169 cases with severe esophageal or airway burns and subsequent complications have been reported. Most of the victims are children. Currently, when a button battery is swallowed, surgery is required to remove it and treat any associated wounds.

Moreover, traditional interventional medical technologies for the gastrointestinal (GI) tract typically involve invasive tethered devices, such as endoscopes, or passive swallowable capsules that offer medical professionals no control over the behavior of the capsule.

Thus, there is a need for improved devices and methods for treatment of the GI tract.

SUMMARY

In one aspect, a method of treatment is provided, including delivering an origami robot in a folded position into a gastrointestinal tract of a patient, causing the origami robot to unfold within the gastrointestinal tract, and directing the origami robot to a site requiring treatment in the gastrointestinal tract.

In another aspect, a system for medical treatment is provided, including an origami robot encapsulated for ingestion by a patient. In some embodiments, the system also includes an external system for magnetically manipulating the origami robot following its ingestion.

In yet another aspect, a method of preparing an origami robot for use in the gastrointestinal tract is provided, including encapsulating the origami robot with a material configured to (i) permit the origami robot to be swallowed by a patient, and (ii) release the origami robot from the encapsulating material in the stomach of the patient.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

DETAILED DESCRIPTION

Origami robots and associated systems, methods of treatment, and methods of manufacture are provided that offer improved non-invasive treatment of the GI tract.

Microsurgical tools that are minimally invasive, degradable, multifunctional, and well accepted by patients are desirable. However, due to difficulty with current treatment procedures, there is a need for miniature surgical tools that, aside from diagnosis, can potentially perform versatile medical or surgical tasks in vivo involving non-invasive transportation and deployment in a targeted location, mechanical operations on tissues or fluids, such as delivery, microanchoring or gripping, removal, cleaning, patching, piercing, sampling, and biodegradability. It has been discovered that origami robots as described herein provide versatile capabilities for gastrointestinal interventions, as they can move and manipulate with a high degree of control and be minimally invasive for the patient.

In particular, a new origami robot that can be swallowed and sent through the esophagus to the stomach has been developed. Once in the stomach, the robot self-deploys and is controllable using an external magnetic held to reach a location of interest where it can use its body to patch a wound or inflammation made by an accidentally swallowed battery, such as a button battery. Origami robot designs have been discovered to be well suited for tasks that require multiple modalities of locomotion, such as traveling through the esophagus and the stomach, because they can traverse the esophagus in a compact shape (e.g., a pill shape) and then morph to enable subsequent tasks (e.g., moving to a wound site and delivering drug or patching the wound) within the stomach and/or intestines. Because the origami robots can be manipulated externally, the robots and methods described herein advantageously provide a non-invasive method for clinical interventions.

One example of clinical interventions where a multifunction miniature robot is desired is in the treatment of patients who have inadvertently or otherwise ingested a button battery. Given the fatality of these accidents and the lack of efficient interventional tools to counteract them, the present disclose involves deploying a miniature biodegradable origami robot in the stomach, guiding the robot to a wound location where it can remove a lodged battery and effectively administer drugs directly to the wound location, and eventually dispose of itself on-site by biodegradation or digestion. Other examples of treatments include wounds and other ailments of the GI tract and stomach, for which the origami robots may deliver drugs and/or provide a wound covering.

Origami robots and associated systems, methods of treatment, and methods of manufacture are described in more detail herein.

Origami Robots & Systems

Figure 1:
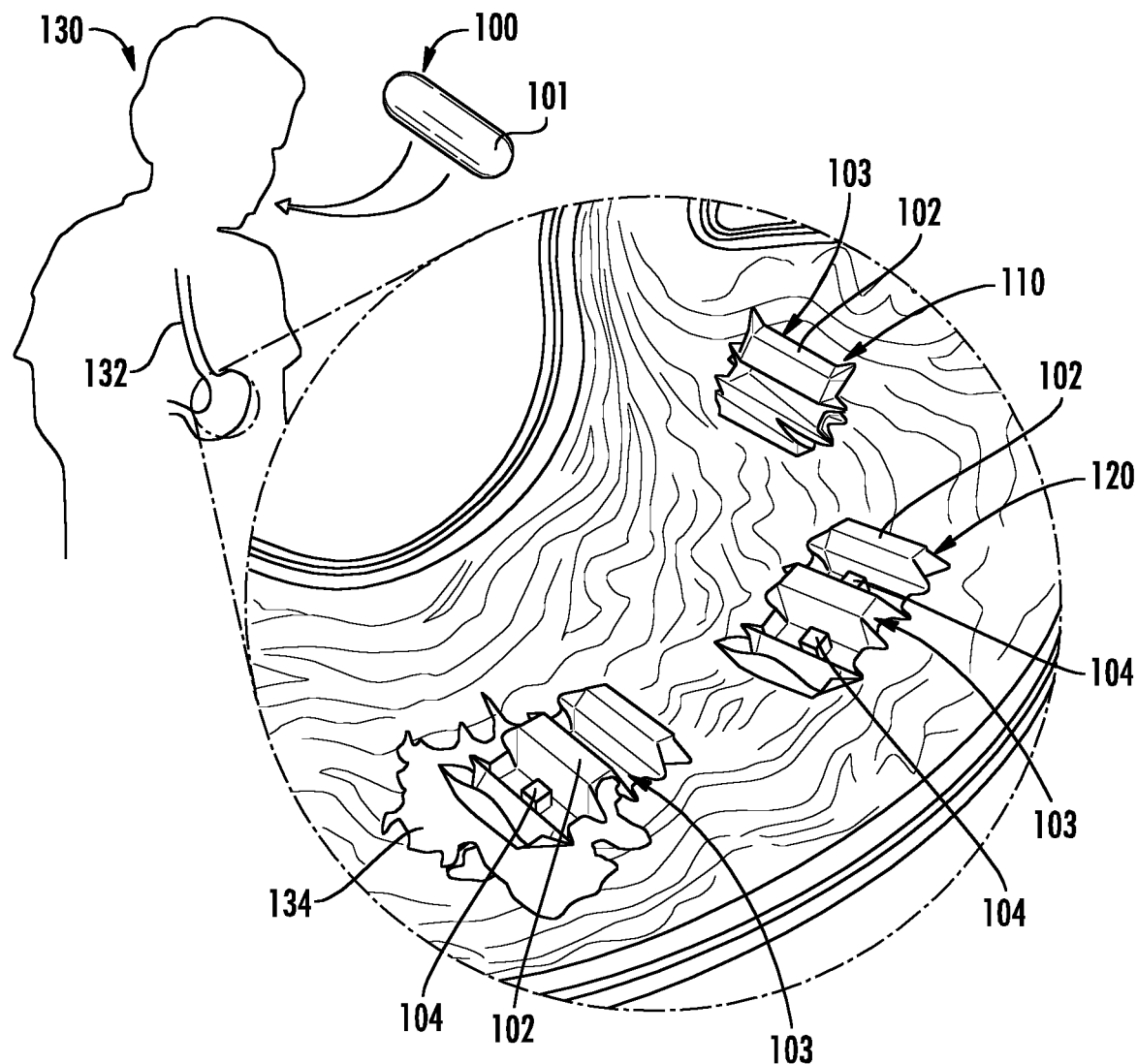
FIG. 1 shows a magnified view of an origami robot deployed in the stomach of a patient.
Figure 2:
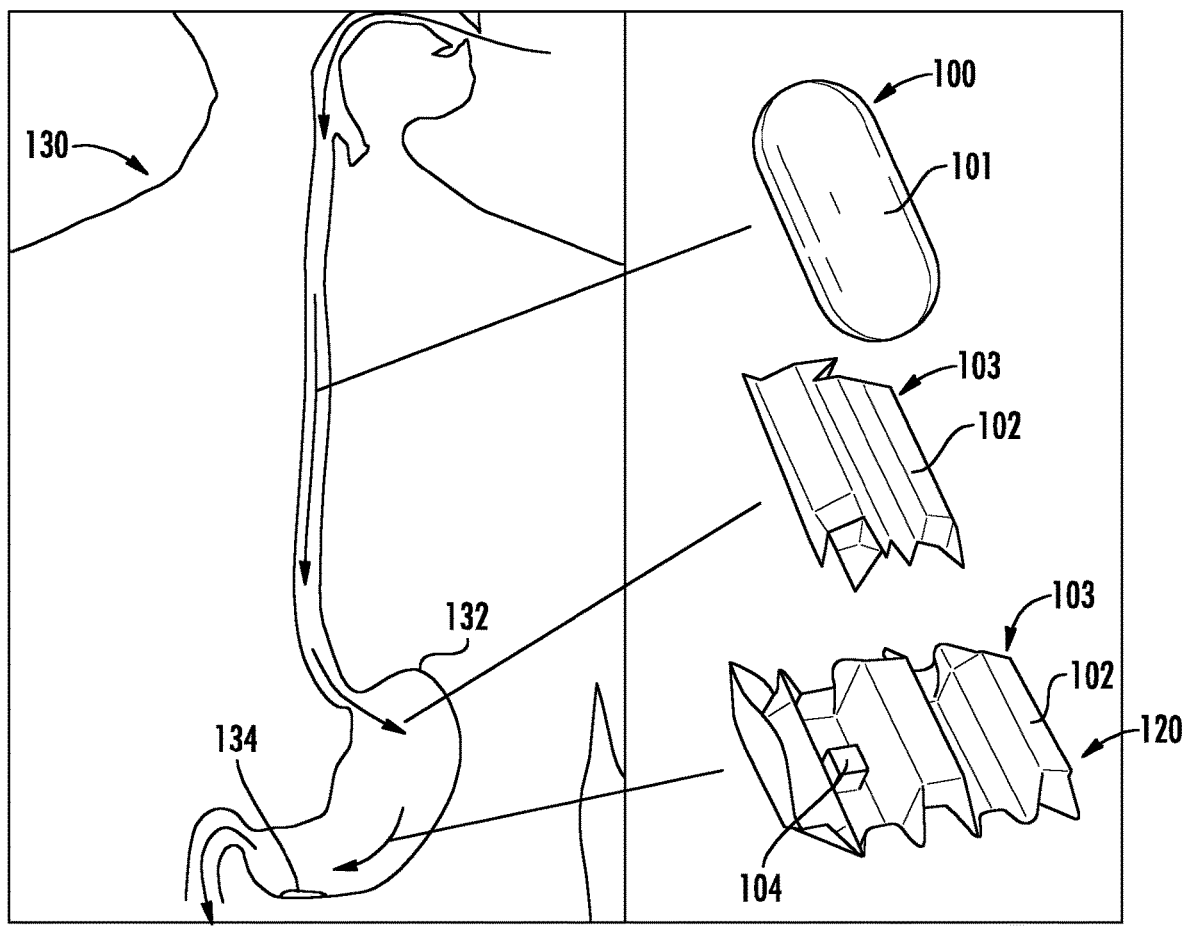
FIG. 2 shows the various stages of an origami robot deployed in the GI tract of a patient.

In certain embodiments, as shown in FIGS. 1 and 2, a system for medical treatment includes an origami robot 103 that is encapsulated for ingestion by a patient 130. As used herein, the phrase "origami robot" refers to a device having a foldable body portion that is configured to perform basic tasks and movements via a combination of folds, slits, patches of material, or other structural features that are designed to respond to manipulation, such as by a magnetic field, heat source, or other mechanism. The origami robot 103 may be a suitable origami robot type device, for example, as described in Miyashita, et al., "An Untethered Miniature Origami Robot that Self-folds, Walks, Swims, and Degrades," 2015 IEEE International Conference on Robotics and Automation (ICRA), which is incorporated by reference herein.

The origami robot 103 may be encapsulated in a biocompatible material 101 that is dissolvable or meltable within the gastrointestinal tract of a patient. That is, the origami robot 103 may be encapsulated by a material 101 that forms an ingestible or swallowable capsule or pill 100 around the origami robot 103. The capsule or pill 100 may be formed in any suitable shape, such as a sphere, spherocylinder, cylinder, or other shape. For example, the origami robot 101 may be encapsulated in a folded position such that the origami robot 103 is configured to unfold following dissolving or melting of the material 101. For example, FIG. 1 illustrates a capsule 100 that is ingested and upon dissolving/melting of the capsule material 101, the origami robot 103 is exposed in a partially folded position 110, and unfolds into an unfolded position 120.

Any suitable biocompatible encapsulation material 101 known in the art may be used to encapsulate the origami robot 103. For example, traditional pharmaceutical capsule materials, such as animal protein (e.g., gelatin) or plant polysaccharides or their derivatives (such as carrageenans and modified forms of starch and cellulose, including hypromellose, a polymer formulated from cellulose). In some embodiments, the biocompatible capsule material 101 is ice.

Ice capsule transportation may provide various benefits over other approaches such as encapsulation by gelatin or sugar. First, ice is safe and reduces friction while sliding through the esophagus by peristalsis. Second, ice disappears quickly and completely in vivo by melting once it reaches the stomach, and thus it doesn't hinder the robot's motions unlike other materials, which has been discovered to be an issue with certain traditional encapsulation materials. Third, ice is easily and cost effectively produced in a freezer.

In other embodiments, the origami robot 103 is encapsulated within a shell that opens in vivo to release the origami robot, not by melting or dissolving, but instead by fracturing or opening into pieces that can pass through the GI tract intact.

The capsule 100 may have any suitable dimensions. In certain embodiments, the capsule 100 has a length in the range of about 15 mm to about 50 mm, such as about 20 mm to about 35 mm, or about 25 mm to about 30 mm. For example, the capsule may have a length of about 27 mm, which is approximately the 000 standard pill size (length of 26.14 mm, diameter of 9.97 mm). In certain embodiments, the capsule 100 has a diameter or height in the range of about 2 mm to about 20 mm, such as about 5 mm to about 15 mm, or about 8 mm to about 12 mm. In one embodiment, the capsule 100 has a length of about 25 mm to about 30 mm and a diameter or height of about 8 mm to about 12 mm. Such dimensions may be suitable for use in adult humans and may be scaled down for use in children.

The size of the capsule 100 may further be selected such that the capsule sinks in water given the particular origami robot's weight. For example, the origami robot may have a weight ($w_r$) in the range of about 0.3 g to about 2 g, such as about 0.4 g to about 1 g, or about 0.5 g to about 0.75 g. In one embodiment, the origami robot weighs about 0.578 g. The weight of the capsule 100 containing the robot may be in the range of about 1 g to about 5 g, such as about 1.5 g to about 4 g, or about 2 g to about 3 g. In an embodiment in which the origami robot weighs about 0.578 g, the capsule 100 may weigh about 2.55 g, with a volume of about $2.22 \times 10^{-6}$ m$^3$.

The capsule material 101 and the shape and size of the capsule 100 may be selected such that the capsule material 101 is configured to dissolve or melt within a few minutes of reaching the patient's stomach. For example, in the embodiment in which the origami robot weighs about 0.578 g, and the ice capsule 100 weighs about 2.55 g, with a volume of about $2.22 \times 10^{-6}$ m$^3$, the ice capsule 100 was found to melt in water in a period of less than a minute to a few minutes, depending on the temperature.

Figure 5:
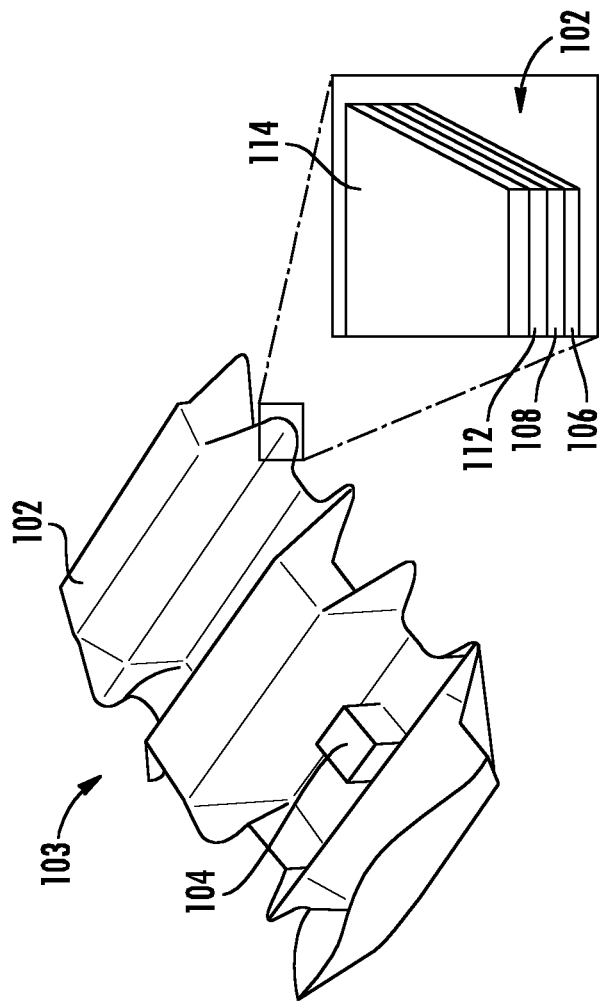
FIG. 5 illustrates an origami robot, including a magnified view of the body portion of the origami robot.

In certain embodiments, as shown in FIG. 5, the capsule material 101 of capsule 100 is dissolved or melted to release origami robot 103, which includes a foldable body portion 102. The foldable body portion 102 may be formed of any suitable foldable materials. In some embodiments, the foldable body portion 102 is formed of at least an actuation layer 106 for self-folding. For example, the actuation layer 106 may be formed of a suitable heat sensitive shrinking film material, such as BIOLEFIN, available from National Shrinkwrap, which deforms at 65° C., or polyvinyl chloride (PVC).

In addition to the actuation layer 106, the foldable body portion 102 may also include one or more structural layers (shown in FIG. 5 as 112, 114). For example, the structural layer may be relatively rigid layers (as compared to the actuation layer), in which slits, creases, or other folding features are formed. In some embodiments, the structural layer is an organic structural layer 112, such as an animal tissue layer. For example, a suitable animal tissue layer may be an intestinal wall layer, such as a pig intestine wall, available from Eastman Outdoors.

Depending on the particular application of the origami robot 103, the foldable body portion 102 may also contain a polyolefin layer 114 and/or a drug carrying layer 108. The drug carrying layer 108 may contain an active pharmaceutical ingredient (API) and be configured to release the API according to a desired release profile. The drug carrying layer 108 may take any suitable form, such as a matrix or other API-impregnated carrier system. In some embodiments, the various layers of the foldable body portion 102 are adhered together by a suitable adhesive material. For example, the layers 106, 108, 112, 114 may be adhered by a silicone adhesive, available from McMaster-Carr. In some embodiments, the layers are laminated by the heat sensitive film of the actuation layer 106.

As described in Miyashita, et al., the body portion 102 may have a symmetrical layer configuration, or the body portion 102 may have an asymmetrical layer configuration. In some embodiments, the body portion 102 is formed of biocompatible and biodegradable materials, such that the body portion biodegrades over time.

In some embodiments, the materials of the layers are selected to provide layer degradation at different time scales such that each layer fulfills its operational requirements at designed time sequences. For example, the organic structural layer is expected to degrade at the slowest speed while the drug containing layer is expected to degrade constantly and release the API.

In some embodiments, in addition to the foldable body portion 102, the origami robot 103 also contains a magnet 104. For example, the magnet may be coupled, directly or indirectly, to a portion of the body portion 102. For example, the magnet 104 may be a neodymium magnet. In one embodiment, as shown in FIG. 5, the magnet 104 is a cubic neodymium magnet having an edge length a=3.2 mm and is fixed near one end of the body portion 102.

In the embodiment shown in FIG. 5, the origami robot 103 includes a foldable body portion 102 having five trapezoidal boxed segments which can be stacked and configured as a hexagonal cylinder by folding. The front and back sides of the body portion 102 are designed as point symmetric, such that an asymmetric friction force is induced along the body axis. Thus, the origami robot 103 can locomote even when flipped. The cubic magnet 104 is contained in the second segment, such that it induces an asymmetric moment of inertia under a periodic magnetic field application. The magnet 104 is concealed when the body 102 is folded to form a hexagonal cylinder for encapsulation in an ice capsule. In certain embodiments, as is discussed in greater detail below, the magnet is configured (i.e., has a size and strength) to retrieve a button battery in the gastrointestinal tract of the patient.

In certain embodiments, the body portion 102 of the robot 103 has a wide surface area that enables it to effectively administer a drug to and/or patch a wound in the stomach. As discussed above, the body portion may have a flat or planar type portion that is folded into an accordion type shape. This folded shape enables the robot to compactly fold and be contained with the capsule material 101 and expand to a surface area five times (e.g., in an embodiment having five sections as described above) larger than the capsule 100 when deployed.

In some embodiments, a system for medical treatment including an origami robot 103 that is encapsulated for ingestion by a patient 130 further includes an external system (not shown) for magnetically manipulating the origami robot following its ingestion. The external system may be an electromagnetic actuation system configured to remotely apply one or more magnetic fields to the capsule or origami robot (depending on whether the capsule has melted/dissolved) to control actuation of the robot. As will be discussed below, the movements of the robot may include rolling type motion and walking type motion (e.g., stick-slip motion).

In certain embodiments, the external actuation system includes one or more coils through which currents can be run to generate magnetic fields of various strengths and directions, through means known in the art. In one embodiment, the external actuation system includes four cylindrical coils, inclined 45°, distanced 25 cm each center to center, surrounding the center of the region in which the magnetic fields are generated, and placed in operable proximity to the stomach. By running currents, a magnetic field of various strength and direction can be generated.

In clinical use, a platform containing the actuation system may be placed in operable proximity to the patient, such as under or near the patient, or a mobile system, such as one or more wands containing the coils, may be used by medical personnel to generate the desired magnetic fields in the stomach of the patient. In clinical applications, one or more of ultrasound, X-ray, and an array of Hall Effect sensors can be used to track the position of the capsule or robot. Such internal imaging systems are well known in the art.

In certain embodiments, the origami robot may contain one or more onboard sensors configured to diagnose the source of internal bleeding or to sense other clinically-relevant properties of the patient's GI tract.

Methods of Treatment

In certain embodiments, methods of treatment utilizing the origami robots described herein include delivering a capsule as described above into a GI tract of a patient and accomplishing one or more clinically-relevant tasks, such as removing a foreign body or patching a wound in the stomach. Both the capsule form of the system and the unfolded origami robot (i.e., after release from the melted/dissolved capsule material) may be manipulated by external means, such as a remote magnetic field.

As used herein, the term "patient" refers to human or other mammalian subjects requiring treatments, including infants, children, and adults.

Generally, methods of treatment utilizing these origami robots involve removing the encapsulation material from the robot, e.g., by dissolving or melting and unfolding the robot like a piece of origami. The unfolded robot moves by virtue of strategically placed folds, slits and/or patches of material that expand or shrink when exposed to heat or magnetic fields. A medical professional pilots the robot from the outside the body using electromagnetic fields to act on an onboard magnet. The robot can also crawl into position by flexing the folds of its body against the walls of the stomach in what is known as stick-slip motion. The robot's biocompatible body can deliver medication to an internal wound or patch it by settling onto the injury. The robot can also use its magnet to "pick up" and remove a foreign object, such as a swallowed button battery. After drug delivery and robot degradation, the magnet may be removed naturally through the gastrointestinal tract.

In one embodiment, the capsule removes a battery or other foreign object from the stomach to prevent further damage of the stomach wall, while the capsule is in its capsule shape. After the patient swallows the ice capsule, the capsule travels by rolling in the stomach, actuated by controlled magnetic fields and guided to the location of the battery. It then grabs the battery by magnetic attraction (via a magnet onboard the robot), and dislocates it from the inflammation site. The magnet-battery distance changes over time due to ice melting, altering the magnitude and direction of torque transmitted to the battery, enabling diverse lift postures. In order to induce maximum torque for the lift, the magnet should orient planarly to the battery rather than perpendicularly. The ice dissolution approach enhances the probability of a proper attachment, as the magnet steadily reorients itself while ice melts to maximize the connection strength. This magnet reorientation while melting also reduces the risk of the magnet and battery magnetically pinching the mucosa.

Figure 6:
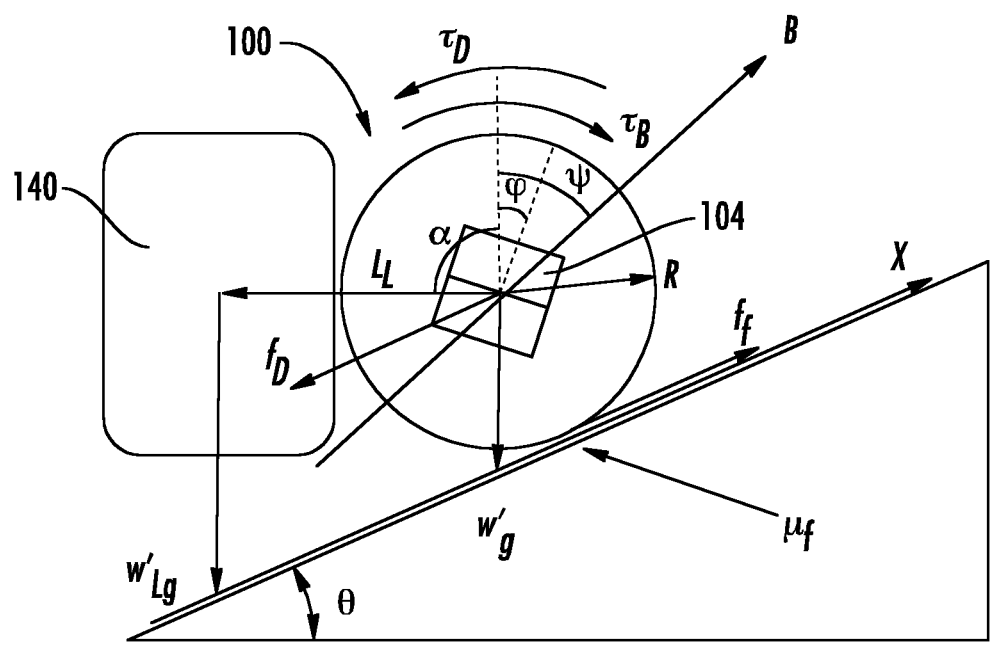
FIG. 6 illustrates the rolling motion mode one embodiment of an origami robot.

In this rolling travel mode, the ice capsule is actuated by applying a rotating magnetic field. FIG. 6 shows a schematic of a magnet 104 of an origami robot in a cylindrical structure (ice capsule) 100 on a slope, carrying a load 140 (e.g., a 303 battery). The slope has an angle θ, and the coordinate X is set along the slope. In this example, the capsule 100 has radius R=5.5 mm, a length L=27 mm, an angle φ from the vertical plane, angular velocity co, coefficient of friction $\mu_f$ with an experience of friction force $f_f$, and mass w=2.55 g where the equivalent mass in water is w'=0.33 g. The load 140 (e.g., button battery) has mass $w'_L$=2.18 g with equivalent mass $w'_L$=1.63 g in water, and can be attached with either the longitudinal face of the battery, in which case the magnet-battery distance $L_L$ will become $L_L$=11.24 mm, or collateral face (as shown in FIG. 6), in which case the magnet-battery distance will be $L_L$=8.19 mm.

The neodymium magnet 104 is cubic and has edge length a=3.2 mm, with dipole moment m=29.8×10$^{-3}$ Am$^2$ in this example and m=a$^3$M$_{sat}$=33.9×10$^{-3}$ Am$^2$ in theory (m=29.8× 10$^{-3}$ Am$^2$ used for calculations), where M$_{sat}$=1.03×10$^6$ A/m is the saturation magnetization of a neodymium magnet. The rotating magnetic flux density has absolute value of B, angle ψ from the vertical plane, and it generates magnetic torque $\tau_B$ on the capsule. Fluidic drag force $f_D$ and torque TD act on the capsule, and g=9.81 m/s$^2$ is acceleration of gravity. It is assumed that the density is homogeneous in the capsule.

The governing equation for the ice capsule to climb the slope underwater was determined, as shown below, and the required B to lift a button battery was investigated. The condition of no-slip motion is $$f_f \leq \mu_f (w' + w'_L) g \cos\theta \quad (1)$$

Acting magnetic torque is $$\tau_B = mB \sin(\psi - \varphi) \quad (2)$$

Equation for motion of translational motion is $$w\frac{d^2x}{dt^2} + W L\frac{d^2 x_L}{dt^2} = f_f - (w' + w'_L) g \sin\theta - f_D \quad (3)$$

where $x_L$ is the x coordinate of the load. Rotational motion is $$(I + I_L)\frac{d^2\varphi}{dt^2} = \tau_B - f_f R - w'_L g L_L \sin(\alpha - \varphi) - \tau_D \quad (4)$$

where I=½wR$^2$ is the moment of inertia of the capsule and $I_L$ is that of the load around the center of the capsule.

Under no-slip condition, $$\frac{dx}{dt} = R\frac{d\varphi}{dt} \quad (5)$$

and $$x_L = x - L_L \cos\left(\frac{\pi}{2} + \theta - (\alpha - \varphi)\right) \quad (6)$$

Thus, the following is obtained $$\frac{d^2 x_L}{dt^2} = -L_L\omega^2 \sin(\varphi - \alpha + \theta) + (R + L_L \cos(\varphi - \alpha + \theta))\frac{d^2\varphi}{dt^2} \quad (7)$$

Based on equations (3)-(7), the following governing equation is obtained $$\left[\left\{\frac{3}{2}wR + \frac{I_L}{R} + w_L(R + L_L \cos(\varphi - \alpha + \theta))\right\}\frac{d^2\varphi}{dt^2} - w_L L_L \omega^2 \sin(\varphi - \alpha + \theta) + (w' + w'_L)g\sin\theta + f_D\right] R - w'_L g L_L \sin(\varphi - \alpha) + \tau_D = mB\sin(\psi - \varphi) \quad (8)$$

With the controlled translational velocity v=32.2 mm/s and an angular velocity of ω=5.85 rad/s, the drag for $f_D$ is $$f_D \sim C_D R L \rho v^2 \quad (9)$$

where $C_D$=1.1 is the drag coefficient with derived Reynolds number 398 and the density of water at 25° C. ρ=1000 kg/m$^3$. The drag force is obtained as $f_D$=1.69×10$^{-4}$ N, which is negligibly small $$\left(\frac{\tau_D}{\tau_B} \ll 1\right).$$

From Navier-Stokes equation and equation of continuity, torque $\tau_D$ acting on the capsule is $$\tau_D \sim 4\pi\mu_D R L \omega \quad (10)$$

where $\mu_D$=0.89×10$^{-3}$ Pa s is the viscosity of the fluid (water, 25° C.). $\tau_D$=9.71×10$^{-6}$ is obtained, which is, again, negligibly small $$\left(\frac{\tau_D}{\tau_B} \ll 1\right).$$

When the rotating magnetic field is applied slowly enough and the motion of the capsule is in steady state, namely when $$\frac{L_L \omega^2}{g} \ll 1 \text{ and } \frac{d^2\varphi}{dt^2} = 0 \text{ hold,}$$

from equation (8) the following is obtained $$\sin(\psi - \varphi) = \frac{(w' + w'_L) gR \sin\theta - w'_L g L_L \sin(\varphi - \alpha)}{mB} \quad (11)$$

$$(\leq 1) \Longrightarrow B \geq \frac{(w' + w'_L)gR\sin\theta - w'_L g L_L \sin(\varphi - \alpha)}{m}\bigg|_{max} = \frac{((w' + w'_L)R\sin\theta - w'_L L_L)g}{m} \quad (12)$$

From equations (3), (5), and (7), $$f_f = wR\frac{d^2\varphi}{dt^2} + w_L\left[-L_L\omega^2 \sin(\varphi - \alpha + \theta) + (R + L_L \cos(\varphi - \alpha + \theta))\frac{d^2\varphi}{dt^2}\right] + (w' + w'_L)g\sin\theta + f_D \quad (13)$$

Referring to equation (1) and above approximations, the following is obtained $$(w'+w'_L)g \sin\theta \leq \mu_f(w'+w'_L)g \cos\theta \therefore \mu_f \geq \tan\theta \quad (14)$$

It has been determined that equations (12) and (14) are the conditions for the ice capsule to satisfy the rolling motion on the slope without slip.

It has been determined that the most difficult situation is confronted when the attachment occurs between the capsule and the side wall of the battery on a non-slope surface ($L_L$=11.24 mm, θ=0), which requires B~5 mT, which is relatively high. However, in an in vivo setting, there exist many other postures to carry a battery, such as having the capsule rotate the battery horizontally rather than lifting it, or having the capsule roll over the battery to dislocate it. Both techniques make it easier for the capsule to relocate the battery.

After the battery 140 is dislodged by the origami robot 103/capsule 100, the battery 140 and the origami robot 103 are removed from the patient's body through the gastrointestinal tract.

Figure 7:
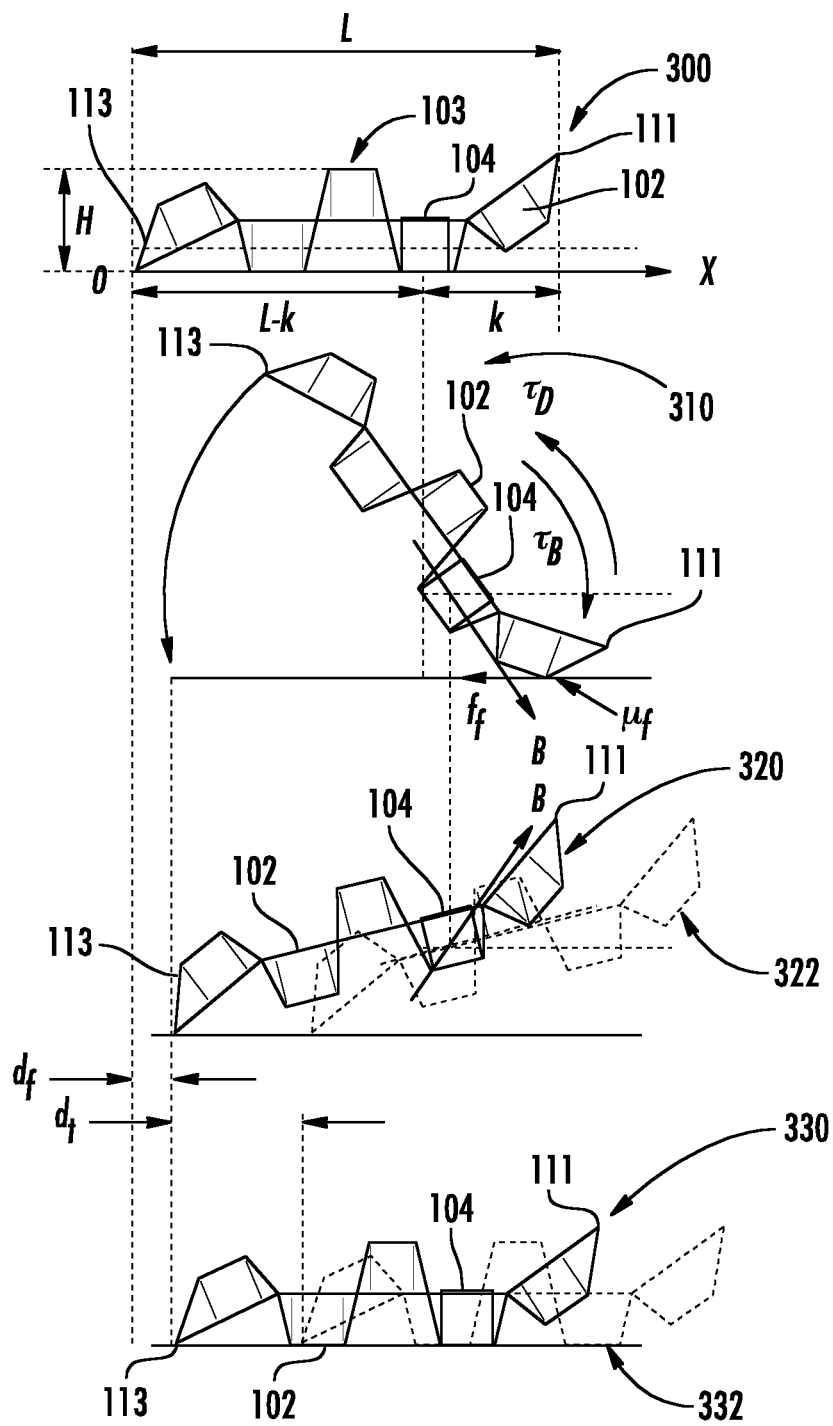
FIG. 7 illustrates the walking motion mode of one embodiment an origami robot.

In some embodiments, as illustrated in FIG. 7, the origami robot 103 may be used to walk in the stomach and patch or heal an inflammation or other wound site by landing on it and/or by releasing a drug to the damaged area through the robot's body degradation. The walking motion is designed based on stick-slip motion on ground, as described in in Miyashita, et al. However, in the present disclosure, the robot acts "underwater" (i.e., submerged in the fluids within the GI tract) and thus experiences effects from moving in a low Reynolds number environment. In contrast to the rolling motion, the walking motion allows the position of the robot to be precisely adjusted on the stomach surface.

For example, as shown in FIG. 7, the magnetic field may be applied (e.g., at 5 Hz) in the direction along which the robot is actuated (positive X direction in the figure) oscillating through four angles (Ψ, Ψ/2, −Ψ/2 and −Ψ; Ψ=1.1 rad is an angle from the horizontal plane). When such an alternating field is applied, the origami robot 103 can "walk forward" due to the combination of thrust, asymmetrical frictional force induced by the shape between front and rear ends (111, 113) of the body 102, and asymmetrical mass balance of the body (due to the off-centered placement of magnet 104 in the second segment from the front end 111 of the body 102). More precisely, one step motion consists of three distinctive phases, including a first phase 300, in which the body 102 lies on the ground, a second phase 310, in which the body 102 points down at a first end 111 following a downward-oriented magnetic field application, and a third phase 320, in which the body 102 points up at the first end 111, following an upward-oriented magnetic field application. After the third phase, the body 102 returns to the initial phase, in which it lies on the ground.

From the first to second phases (300 to 310), the body 102 lifts up the rear end 113 while the front end 111 is still in contact, keeping the anchor position against thrust and exploiting the friction (i.e., stick motion). The center of mass, assumed to be at the location of the magnet 104, travels forward at distance of ~k(1−cos Ψ), where k=8.7 mm is the distance between the center of the magnet and the front edge 111 of the body 102.

From the second to the third phases (310 to 320), as a turn of magnetic field occurs instantly, and due to the relatively low Reynolds environment with negligibly light body mass compared to the magnet mass, the body is expected to rotate about the magnet keeping the height of the center of mass (i.e., slip motion). Due to the body balance shifted to the front and also depending on the frequency of B, the posture does not completely catch up to the magnetic field, compared to the posture in the second phase (310). Considering the thrust that acts to push the body backward, this angle of magnetic field pointing up is better minimized. Position 322 illustrates the expected position of the body portion considering thrust. However if Ψ is set very small, for example ~0, the chance that the robot 103 stumbles on mucosa increases.

From the third to the fourth phases (320 to 330) (the fourth phase 330 is the same state as the first phase), the body portion 102 exploits friction and low stroke, and enables further body travel. Position 332 illustrated the expected position of the body portion considering thrust. In FIG. 7, $d_f$ represents the distance travelled by asymmetric friction, while $d_t$ represents the distance travelled by thrust.

In one example embodiment, the body length is L=34.3 mm, the height H=7.8 mm, and the width W=16.7 mm. The traveling distance D in one cycle without considering thrust is kinematically derived and is $$D \approx L - k\cos\psi - (L-k)\cos\left(\sin^{-1}\left(\frac{k\sin\psi}{L-k}\right)\right) \qquad (15)$$

With this function, the walking speed of the robot 103 is estimated to be 2.98 cm/s. As the experimental results discussed below show the walking speed to be 3.71 cm/s, the difference may be due to the influence of thrust.

Thus, a combination of capsule rolling and robot walking motions may be used to achieve the desired behavior of the capsule/robot. In particular, the motions may be achieved using a suitable remote magnetic field applied to the capsule/robot within the patient's GI tract.

In certain embodiments of the treatment methods disclosed herein, the wound is at least partially formed by an ingested button battery, and the method includes removing the button battery from the site. For example, as discussed above, removing the robot may remove the button battery from the site when it is still encapsulated in the capsule material, via a rolling motion. Alternatively, the robot may remove the button battery from the site when it is in an un-encapsulated, or unfolded, state.

In certain embodiments in which the body portion 102 includes an API in one or more of the layers forming the body, the method of treatment includes releasing the API to the site requiring treatment. For example, the layer containing the drug may include a matrix material or other material in which the API is disposed, and which controls the release of the API from the layer. Such controlled release matrix materials and drug combinations are known in the art.

In certain embodiments, as discussed above, the step of causing the origami robot to unfold involves dissolving or melting the encapsulation material.

In certain embodiments, delivering the origami robot to the gastrointestinal tract involves injecting the origami robot into the gastrointestinal tract or the patient swallowing the origami robot.

In certain embodiments in which the origami robot is deployed to treat a wound within the stomach of the patient, as shown in FIG. 1, the method of treatment includes the body portion 102 of the origami robot 103 settling at the site requiring treatment to patch a wound 134 at the site.

In certain embodiments, the methods of treatment described herein, utilizing a capsule containing an origami robot, may be used in conjunction with known medical imaging technologies.

Methods of Manufacture

Methods of manufacturing the origami robots and capsules described herein are also provided. In certain embodiments, a method of preparing an origami robot for use in the gastrointestinal tract includes encapsulating the origami robot with a material configured to (i) permit the origami robot to be swallowed by a patient, and (ii) release the origami robot from the encapsulating material in the stomach of the patient. The origami robot and capsule materials may include any of the varieties, features, and combinations of features described herein.

The body portion 102 of the origami robot 103 may be manufactured to contain one or more folds, slits, or patches of material configured to expand or shrink when exposed to heat or a magnetic field, to induce motion of the origami robot, such as described by Miyashita, et al.

Once the body portion 102 is manufactured to contain the desired fold features, it may be folded for encapsulation. In certain embodiments, the body portion 102 is folded by exposing the origami robot 103 to heat, such that the actuation layer (e.g., heat sensitive film) is caused to shrink and fold the body portion 102. In one embodiment, the self-folding process includes placing the robot 103 on a hot plate. For example, in the examples below, when the layered flat body was exposed to heat of 100° C., the BIOLEFIN layer shrunk causing the entire structure to fold itself into the final configuration without human intervention. Beneficially, while the materials forming the body are biodegradable, the entire body keeps its shape despite the temperature.

In certain embodiments, the encapsulated origami robot 103 is folded such that upon release of the origami robot 103 from the encapsulating material 101 in the stomach of the patient, the origami robot 103 unfolds into its original position.

The origami robot 103 may be encapsulated in a material via known encapsulation mechanisms. For example, for an ice capsule, the robot 103 may be placed in a silicone mold that is filled with water and frozen, to produce an ice capsule 100.

The embodiments of the present disclosure will be better understood with reference to the following non-limiting examples.

EXAMPLES

Artificial Stomach Fabrication

A physical environment for testing the performance of the origami robot systems described herein was created. The physical environment included an artificial esophagus and a silicone stomach that feature a biologically-comparable stiffness and folded lining inside, including artificial mucosa. The stomach is a muscular and hollow organ of the digestive system, responsible for breaking down food. Following the size specifications of an average human stomach, the stomach has a maximum width of 10 cm. The stomach environment was reproduced using a template silicone mold technique to be mechanically analogous to the real tissues. The artificial organs (1) provided a nonperishable, realistic, cost-effective environment for iterative tests of the structure and function of the robot, and (2) allowed easy parameterization of the artificial environment, such as the size of the organs and location of the damaged area. Thus, emphasis was placed on the mechanical attributes of the stomach such as structure, stiffness, friction, fluid viscosity, and color, while other properties such as temperature, pH, peristaltic motion of the esophagus, or volumetric dynamics of the stomach were omitted.

To define the design guidelines necessary to simulate the real environment, the stiffness of pig stomach samples were experimentally investigated. The compressive and tensile stresses of rectangular pig stomach samples ($15 \times 30 \times 5$ mm$^3$, length×width×height) were measured using an Instron Machine (Instron 5944). For compressive stress, a rectangular iron bar with a contact area of $11 \times 14$ mm$^2$ was used to apply pressure to the tissue, and for tensile stress, grippers with a rough surface (built using rapid prototyping) of size $40 \times 30$ mm$^2$ were used to grip the slippery tissues when stretched. The pig's stomach was fresh (within 24 hours from collection) and preserved at −4° C. before being used.

Figure 4:
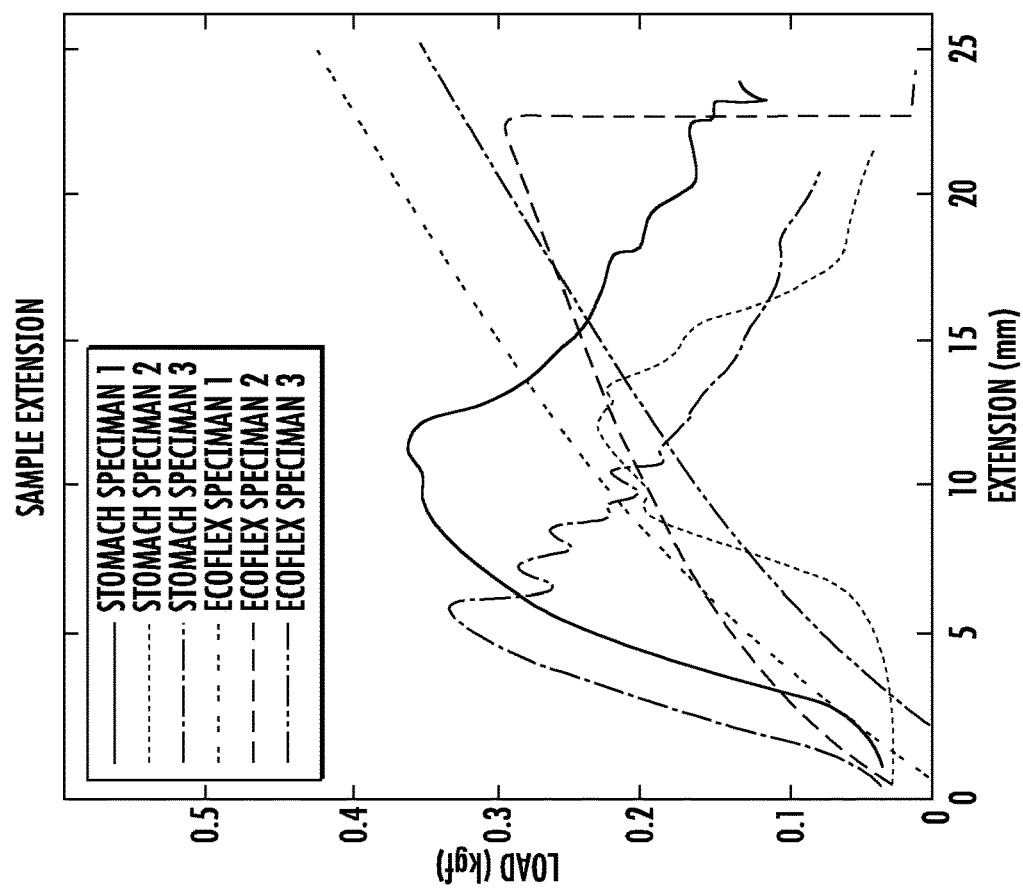
FIG. 4 is a graph showing the extension versus load of various samples, as described in the Examples.
Figure 3:
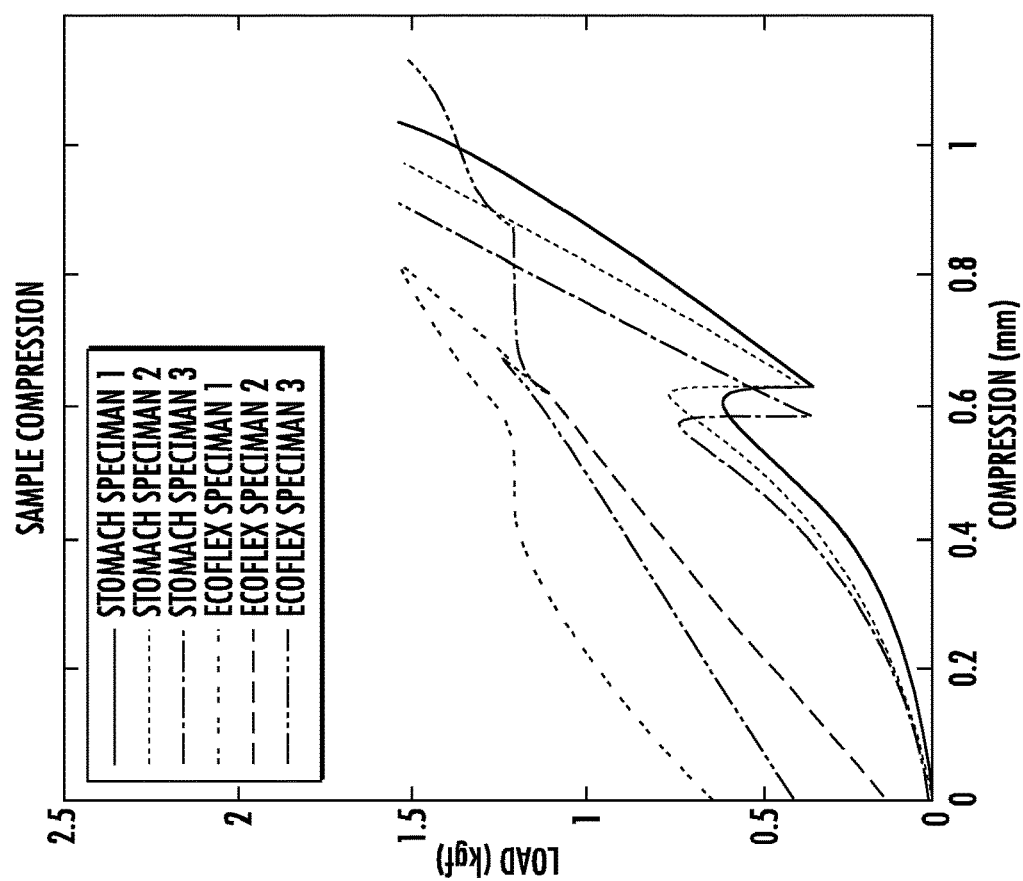
FIG. 3 is a graph showing the compression versus load of various samples, as described in the Examples.

FIGS. 3 and 4 are plots characterizing the stiffness properties of the biological and artificial stomach tissues, depending on the mechanical deformation applied, i.e., compressive and tensile stress, are shown. The average fitted lines for the biological stomach profiles were computed, resulting in the equations S [kgf]=0.72 C [mm]−1.06 and S [kgf]=0.04 E [mm]−0.19 for compression and extension, respectively. In the case of the biological stomach, only the initial tissue deformation depicted by the first increasing curve was considered, given the limited tissue deformation capabilities expected from the origami robot. These values were most closely matched with ECOFLEX 00-30 molding silicone, available from Smooth-On, Inc., which showed average fitted lines of S [kgf]=1.03 C [mm]+0.68 and S [kgf]=0.01 E [mm]+0.07 for compression and extension, respectively, as shown in FIGS. 3 and 4. These equations show that a reasonable match between the stiffness of the biological and artificial stomach samples was achieved.

The mold templates of the esophagus and stomach were 3D printed (Fortus by Stratasys, 250 mc and 400 mc) referring to a market available CAD model (Turbosquid). First, 3D printed molds of the outer and inner parts of the stomach and esophagus were made. The inside mold was used to create a reverse mold of the lining. This latter mold and the outside part were used to compose the final product. MOLD STAR 15 SLOW (available from Smooth-On, Inc.) was used to fabricate the reverse mold. The final product is made of ECOFLEX 00-30 to match the stiffness of the pig's stomach. The stomach wall has a thickness ranging between 3.5 and 5.5 mm due to ridges of mucosa.

In general, the stomach is filled with gastric fluid and the walls of both esophagus and stomach are lubricated with mucosa secretion and body fluids. Though the viscosity of gastric fluid shall vary, when the stomach is filled with water, its viscosity can be approximated as 1 centistoke. For the investigation of the biodegradability of the origami robot, described below, market available Simulated Gastric Fluid (available from Fisher Scientific), which contains 0.2% sodium chloride in 0.7% hydrochloric acid solution (pH: 1.0-1.4), was used.

Ulcer Formation

This experiment assessed the prospective damage of the stomach wall caused by a button battery that was accidentally ingested. In order to reproduce realistic inflammation of the tissue, a damaged area of an ex vivo tissue was created using a button battery. A button battery (303 battery, 175 mAh) and tissue (ham slice, 2.3 mm thickness) was sandwiched between two acrylic plates for 60 minutes.

After a few minutes, air bubbles were observed at the interface between the battery and the tissue due to an electric current flow. In 30 minutes, degradation of the tissue was observed from the opposite side of the tissue. In 60 minutes, a hole of 12 mm diameter was created, clearly displaying the danger of accidental ingestion.

Biodegradability of the Origami Robot

An origami robot 102 as illustrated in FIG. 5 was manufactured. The foldable body portion 102 included a multi-layer structure containing an actuation layer of BIOLEFIN, a polyolefin layer, a structural layer of pig intestine wall, a simulated drug carrying layer of oblate, and silicone adhesive adhering the layers.

The origami robot was partially placed in simulated gastric fluid set at body temperature (37° C.) for 3 hours and showed signs of degradation over this period. Although the process took a while, and the remains of the origami robot (including the magnet, if present) are expected to be expelled from the body in time, the entire process shows that the presence of the origami robot as a foreign body has less potential to harm the gastrointestinal tract. In a patient's stomach, there exist enzymes such as pepsin, which should accelerate the degradation speed. For safety, no more than two magnets should be in the gastrointestinal tract at the same time.

Origami Robot Deployment Via Capsule Melting

Origami robots as described above in the Biodegradability section, containing one battery, were manufactured and encapsulated in ice, with the resulting capsule having a volume of about $2.22 \times 10^{-6}$ m$^3$. The capsule was tested for melting in liquids at a room temperature of 20° C., though the dissolution time that the ice capsule requires varies depending on the water temperature. According to these tests, it took about 3 minutes at 22° C., and about 1 min at 28° C. (sample number=5) for the ice capsule to melt. Water at body temperature should accelerate the speed. Immediately after ice capsule melting, the robot's body started to be deployed because of the elastic origami hinges of the actuation layer as the body is exposed to water. Once the robot regained its original (i.e., unfolded) form, it showed a stable motion underwater under the application of a magnetic field, as described in more detail below.

Ice Capsule's Rolling Motion and Foreign Body Dislocation

The ice capsule dislocating a button battery from the battery-caused inflammation site was tested. As soon as the ice capsule that contained the origami robot was manually transported to the stomach (at time 00:00), the capsule was actuated for rolling motion by an external magnetic field and visually guided to the button battery location. The ice capsule then reached and connected to the battery, and subsequently successfully dislocated the battery from the spot after several attempts with rolling motion (at time 00:16-00:20). During the operation, the ice melted and continuously reduced the distance between the magnet of the origami robot and the button battery, assisting torque inductions of different magnitudes and angles. Once the coupling between the ice capsule and battery was made, they could be discharged out of the body naturally through the gastrointestinal tract.

Wound Patching by the Origami Robot

An ice capsule as described above was transported through an esophagus (at time 00:00) and melted in water (23° C.) in the stomach, the origami robot regained the target body form (i.e., unfolded) (at time 02:46), walked to the desired site via manipulation by external magnetic fields (at time 03:57), and patched (i.e., floated over the target location) a simulated ulcer (at time 04:04). It was observed that sometimes air bubbles hindered the origami robot from deployment, and thus the robot was left to tumble for a short duration (occurred between 02:46 and 03:57). The process was iterated five times and obtained an average duration of procedure completion of about 5 min. This demonstration proves that a biodegradable artificial robot can be dispatched into the artificial stomach to accomplish a mechanical task for a medical purpose.

Thus, origami robots have been developed that are ingestible and can be controlled to move, manipulate, and accomplish clinically-relevant tasks, such as removing a foreign body and patching a wound in the stomach. The present approach requires no or limited onboard electronics, which allows robot minimization for minimally invasive clinical intervention, and greater flexibility and control in the choice of composite materials to fabricate biocompatible and biodegradable robots that can operate in vivo. Additionally, by embedding origami capabilities, the robot can further facilitate reconfigurability for minimal space occupancy and for accomplishing versatile mechanical tasks as controlled by an external remote magnetic field. The capabilities of the robot can be further augmented by incorporating imaging techniques for trajectory tracking during clinical interventions.

Several design, fabrication, modeling and control challenges were discovered in manufacturing and testing the origami robots, including: (1) miniature robot body design, bypassing the integration of conventional electronics; (2) method of intact, instant, and compact transportation to an affected area and minimum invasiveness of the robot; (3) soft and 2D material selection, deployment and (mechanically) functional robot design; (4) method of non-invasive remote control signal transmission and remote actuation; and (5) after-operation in situ removal or biodegradable material selection. As described herein, these challenges have been overcome by one or more of the following: (1) the described material composition for a biodegradable and biocompatible robot; (2) ice encapsulation of the robot for safe transportation into the stomach; (3) deployable origami body design for wide range affected area coverage, fit-in-capsule origami robot design and fabrication, and integrating a drug delivery layer into the robot; (4) remote magnetic control for rolling and underwater walking; and (5) physics modeling and analysis of robots dynamics.

Advantageously, the miniature robots described herein can carry out versatile clinical procedures inside the body under the remote instructions of medical professionals. These origami-based robots can be ingested into the stomach, locomote to a desired location, remove a foreign body, deliver drugs, and biodegrade for non-invasive removal. Importantly, these origami robots provide the ability to remove objects from a patient's GI tract without traumatic surgery.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of preparing an origami robot for use in gastrointestinal tract, comprising:
    constructing the origami robot such that it comprises a foldable body portion that comprises one or more folds, slits, or patches of material configured to move in response to stimulus external to the patient, to induce locomotion of the origami robot;
    exposing the foldable body portion to heat effective to shrink and/or fold the origami robot to a size suitable for encapsulation, and
    encapsulating the origami robot in a folded position with an encapsulation material configured to (i) permit the origami robot to be swallowed by a patient, and (ii) release the origami robot from the encapsulation material in the stomach of the patient, such that the origami robot unfolds to an operable, unfolded position by removing the encapsulation material.

2. The method of claim 1, wherein the encapsulation material comprises a biocompatible material that is dissolvable or meltable within the stomach.

3. The method of claim 2, wherein the encapsulation material comprises ice.

4. The method of claim 1, wherein the one or more folds, slits, or patches of material are configured to expand or shrink when exposed to heat or a magnetic field, to induce the locomotion of the origami robot.

5. The method of claim 1, wherein the foldable body portion comprises an actuation material layer and a structural material layer.

6. The method of claim 5, wherein the actuation material layer comprises a heat sensitive film.

7. The method of claim 5, wherein the structural material layer comprises an organic animal tissue material.

8. The method of claim 5, wherein the foldable body portion further comprises a layer comprising an active pharmaceutical ingredient configured to be released following ingestion of the origami robot.

9. The method of claim 1, wherein the origami robot comprises a magnet configured to retrieve a button battery in the stomach of the patient.

10. A method of preparing an origami robot for use in gastrointestinal tract, comprising:
encapsulating the origami robot in a folded position with an encapsulation material configured to (i) permit the origami robot to be swallowed by a patient, and (ii) release the origami robot from the encapsulation material in the stomach of the patient, such that the origami robot unfolds to an operable, unfolded position by removing the encapsulation material,
wherein the origami robot comprises a foldable body portion that comprises one or more folds, slits, or patches of material configured to move in response to a stimulus external to the patient, to induce locomotion of the origami robot, and
wherein the encapsulation material comprises a biocompatible material that is dissolvable or meltable within the stomach.

11. The method of claim 10, wherein the encapsulation material comprises ice.

12. The method of claim 10, wherein the one or more folds, slits, or patches of material are configured to expand or shrink when exposed to heat or a magnetic field, to induce the locomotion of the origami robot.

13. The method of claim 10, wherein the foldable body portion comprises an actuation material layer and a structural material layer.

14. The method of claim 13, wherein the actuation material layer comprises a heat sensitive film.

15. The method of claim 13, wherein the structural material layer comprises an organic animal tissue material.

16. The method of claim 13, wherein the foldable body portion further comprises a layer comprising an active pharmaceutical ingredient configured to be released following ingestion of the origami robot.

17. The method of claim 10, wherein the origami robot comprises a magnet configured to retrieve a button battery in the stomach of the patient.

\* \* \* \* \*